(12) United States Patent
Pomati

(10) Patent No.: US 12,042,240 B2
(45) Date of Patent: Jul. 23, 2024

(54) AUGMENTED REALITY USING EYE TRACKING IN A ROBOT ASSISTED SURGICAL SYSTEM

(71) Applicant: Asensus Surgical US, Inc., Durham, NC (US)

(72) Inventor: Stefano Pomati, Meda (IT)

(73) Assignee: Asensus Surgical US, Inc., Durham, NC (US)

( * ) Notice: Subject to any disclaimer, the term of this patent is extended or adjusted under 35 U.S.C. 154(b) by 223 days.

(21) Appl. No.: 16/931,430

(22) Filed: Jul. 16, 2020

(65) Prior Publication Data

US 2021/0038329 A1 Feb. 11, 2021

Related U.S. Application Data

(60) Provisional application No. 62/874,976, filed on Jul. 16, 2019.

(51) Int. Cl.
| | |
|---|---|
| *G09G 5/00* | (2006.01) |
| *A61B 34/00* | (2016.01) |
| *A61B 34/37* | (2016.01) |
| *A61B 90/00* | (2016.01) |
| *G06F 3/01* | (2006.01) |

(52) U.S. Cl.
CPC .............. *A61B 34/37* (2016.02); *A61B 34/74* (2016.02); *A61B 34/76* (2016.02); *A61B 90/361* (2016.02); *G06F 3/013* (2013.01)

(58) Field of Classification Search
CPC ... G06F 3/013; G06F 3/0485; G02B 27/0093; G02B 2027/0138; G02B 2027/0187; G02B 27/017; A61B 1/00048; A61B 1/0005; A61B 3/113; A61B 5/7445; G16H 20/40; G16H 40/63; H04N 7/147
See application file for complete search history.

(56) References Cited

U.S. PATENT DOCUMENTS

| | | | |
|---|---|---|---|
| 2009/0248036 A1* | 10/2009 | Hoffman | A61B 34/30 606/130 |
| 2018/0032801 A1* | 2/2018 | Gur | G06N 20/10 |
| 2019/0179418 A1* | 6/2019 | Marggraff | G06F 3/04842 |

* cited by examiner

*Primary Examiner* — Insa Sadio

(57) ABSTRACT

A system augments a surgical procedure by providing information to the user about regions of a surgical site the user is viewing on a displayed endoscopic image. The system uses an eye tracker to determine the region of the displayed image being viewed by the user, and applies computer vision to the image data to identify structures, conditions or disease states within the region. The system provides information to the user, generates alerts, or modifies operational settings for surgical devices based on the identified structures, conditions or disease states.

14 Claims, 3 Drawing Sheets

AUGMENTED REALITY USING EYE TRACKING IN A ROBOT ASSISTED SURGICAL SYSTEM

This application claims the benefit of U.S. Provisional Application No. 62/874,976, filed Jul. 16, 2019.

TECHNICAL FIELD OF THE INVENTION

The present invention relates generally to the field of surgical robotic systems.

BACKGROUND

U.S. Pat. No. 10,251,713, which is owned by the owner of the present application and which is incorporated herein by reference, describes a robotic surgical system that includes an eye tracking system. The eye tracking system detects the direction of the surgeon's gaze and enters commands to the surgical system based on the detected direction of the gaze.

FIG. 1 is a schematic view of the prior art robotic surgery system 10 of the '713 patent. The system 10 comprises at least one robotic arm which acts under the control of a control console 12 managed by the surgeon who may be seated at the console. The system shown in FIG. 1 includes multiple robotic arms 11a, 11b, 11c. Three such arms are shown but a larger or smaller number may be used. Each robotic arm can support and operate a surgical instrument 9a, 9b, 9c for use on a patient 13. One of the instruments is preferably a camera which records the operating field inside the patient, while the other instruments may be known surgical tools 15, 16.

The arms 11a, 11b, 11c are operated by an electronic control unit 30 which causes the arms to perform the movements entered via the console 12. The unit 30 will receive the high-level movement commands (for example, desired position and inclination of the tool supported by the robot) and will execute them, converting them into the corresponding sequences of signals to be sent to the individual motors of the robot arm articulations. Other details of the system 10 are found in the '713 patent which is fully incorporated herein by reference.

The console includes input devices 17, 18 which can be gripped by the surgeon and moved so as to deliver instructions to the system as to the desired movement and operation of the instruments supported by the arms 11a, 11b, 11c.

The surgeon's movements are suitably reproduced by the surgical instruments by means of movement of the robotic arms. The input devices may be equipped to provide the surgeon with tactile haptic feedback so that the surgeon can feel on the input devices 17, 18 the forces exerted by the instruments on the patient's tissues.

Each input device will typically operate a robot arm. The '571 application describes that where there are two input handles and more than two arms carrying instruments, the system includes a control on the console that allows the surgeon to assign each arm to a desired instrument. This allows a surgeon to control of two of the surgical instruments disposed at the working site at any given time. To control a third instrument disposed at the working site, one of the two handles 17, 18 is operatively disengaged from one of the initial two instruments and then operatively paired with the third instrument.

The console may also include a keyboard 19 and/or touch screen and/or other command input devices. These other command devices might include a pedal device 20, and a button(s) on or in proximity to one or both handles of the input devices 17, 18.

The console 12 has an eye movement tracking system 21 or so-called "eye tracker" for detecting the direction of the surgeon's gaze towards the console and for controlling the surgical system depending on the gaze directions detected. In this way, the surgeon may control functions of the system by means of movement of his/her eyes.

The tracking system estimates the direction of the surgeon's gaze towards the display 22 and performs selection of the commands associated with a zone when it detects a gaze direction which falls within this zone. In one particular example, the commands associated with selection areas 29 on the display 22 comprise the commands for assigning particular ones of the arms to the surgeon input devices. That allows the surgeon to alternate control of the robot arms on the two input devices without letting go of the input devices, but instead by simply looking at the corresponding selection areas on the screen. For example, while controlling each of the arms 11a, 11c with one of the input devices 17, 18, the user might re-assign input device 17 over to arm 11b in order to use or reposition the instrument 9b within the body. Once the task involving movement of instrument 9b is completed, the surgeon can rapidly re-assign input device 17 back to robot arm 11a. These steps can be performed by using the eye tracking features to "drag and drop" icons on the console display towards icons representing the various arms.

In another example described in the '713 patent, the eye tracking system is used to move the camera based on where the surgeon is looking on the display 22. When this function is enabled (e.g. by entering an input command, such as through pressing of a button on the console, depressing a foot pedal, etc), the movement of the eyes over the image of the operating field on the screen causes the movement of the robot arm supporting the camera. This can be used to place the zone the surgeon focused on at the center of the display screen.

The '713 also describes use of the eye tracker to detect the distance between the screen and surgeon's eyes as a way to allow the surgeon to "zoom" the camera display in or out. The system enlarges the picture of the operating field shown on the screen depending on a variation in the distance detected. With this feature, the surgeon can intuitively perform enlargement of the picture by simply moving his/her face towards the screen and, vice versa, increase the viewing area of the operating field, thus reducing enlargement, by moving his/her face away from the screen.

This application described using the eye-tracker of the console (or another eye tracker) to aid in providing an "augmented reality" to the surgeon, by helping to display for the surgeon advanced information at a location on the image display that is most advantageous to the surgeon or most relevant to the type of information being represented.

DETAILED DESCRIPTION

Figure 1:
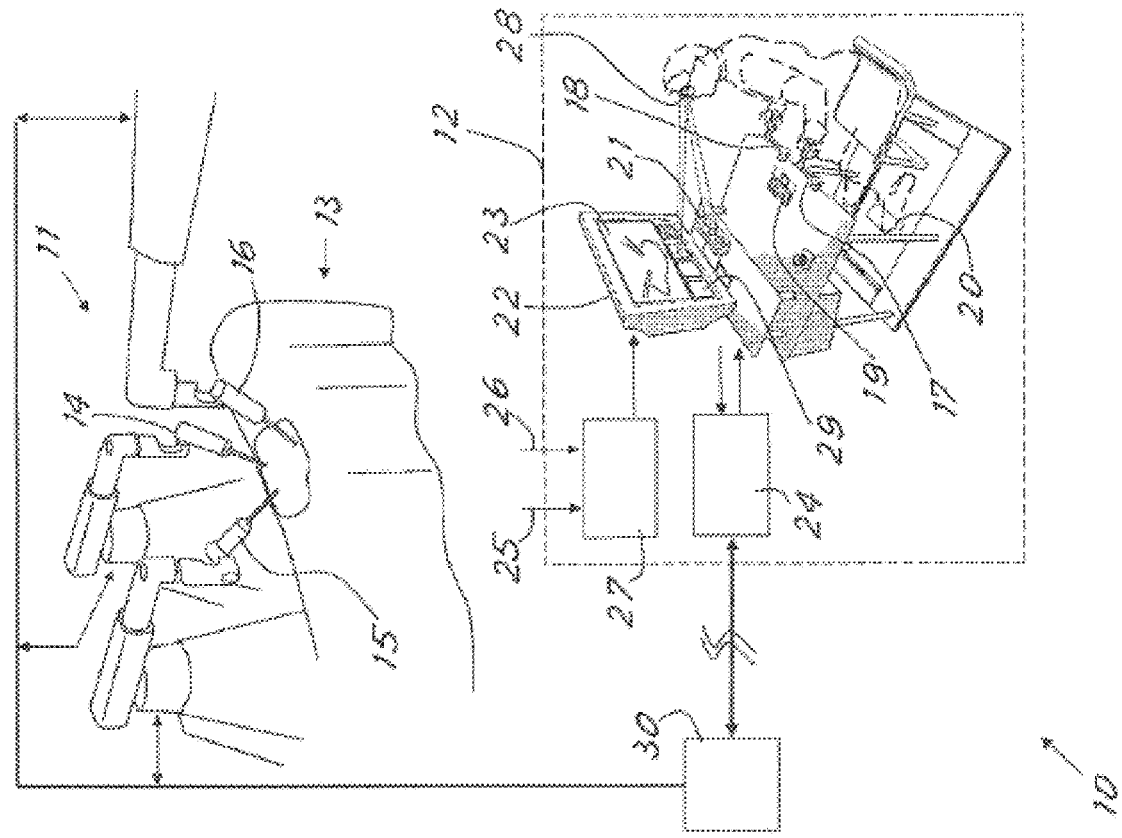
FIG. 1 is a schematic view of a robotic surgery system.

The system will be described in the context of a surgical system of the type described in the Background and shown in FIG. 1, however it should be understood that the disclosed concepts may be implemented on alternative systems without deviating from the scope of the invention.

An exemplary system includes an eye-tracker positioned at the surgeon console. As discussed in the Background, input from an eye-tracker at the surgeon console allows a processor of the system to determine the part of the screen at which the user/surgeon is looking. A processor of the system is further programmed with a computer vision/image processing algorithm that causes the processor the analyze real time images captured using a camera disposed in the patient body cavity in which the surgery is being performed.

Figure 2:
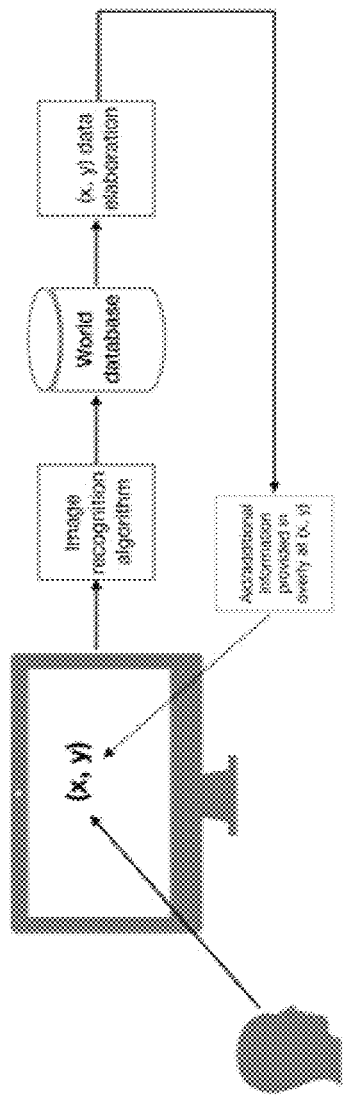
FIG. 2 schematically illustrates use of the disclosed system.

The processor is further configured to interact with a database or a knowledge base (e.g. local or cloud based) storing data which may be compared with the real time image data and used to identify certain features, conditions or events within the body cavity. As depicted in FIG. 2, if real time image analysis/recognition is performed and the system is connected to a database or a knowledge base (e.g. local or cloud based), that information (gaze of the surgeon and surgical image) can be used to compare the current surgical image and the stored data and provide some "augmented reality" in the form of an overlay on the image display in the area at which the surgeon is looking.

More specifically, input from the eye tracker allows determination by the processor as to where on the displayed image the surgeon is looking at and where s/he is going to move the surgical instruments carried by the robotic manipulator. With that information, the processor can cause the following steps to be carried out:

(1) The system recognizes when the surgeon has moved his eyes to a new area of the screen (2) Using image data from the camera, the processor responsible for image processing identifies structures or conditions within the region of the body cavity that corresponds to the area of the screen being viewed by the surgeon. For example, the processor may identify blood vessels, organs, tissue, tissue types, structures or regions to be avoided, tumors or other disease states.

(3) The System takes an action, which may include any of, or multiple ones, of the following actions:

a. Alerts

Figure 3:
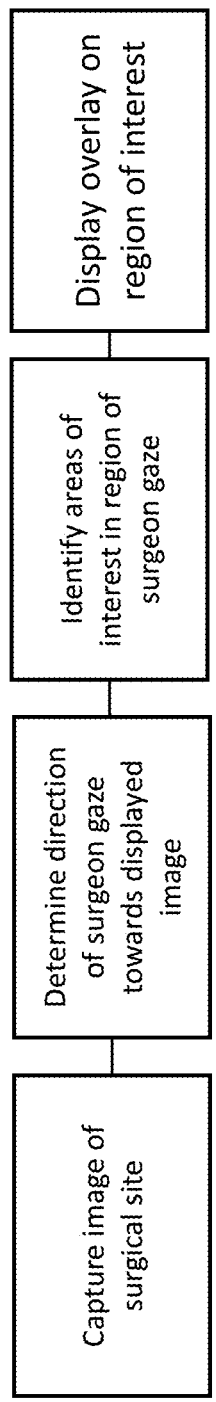
FIG. 3 is a functional block diagram showing one embodiment of a method of using augmented reality with eye tracking.

The system generates an alert that alerts the surgeon to the presence of tissue/structures to avoid in the area at which the surgeon is looking. Alerts may include auditory alerts, overlays or graphics, icons or text displayed on the image display. Preferable displayed visual alerts are caused to appear in the region at which the surgeon is looking so that the surgeon does not need to turn his/her eyes away from the region of interest in order to view them. See the functional block diagram shown at FIG. 3.

b. Information

The system display information to the surgeon relating to the viewed area, helping him/her understand what s/he is viewing. The information might identify the items listed in (2) above using text displayed on the image display.

c. Active Assistance

Depending on what is identified using the image processing, the processor may take an action that facilitates a predicted subsequent surgical task. For example, it may:

Enable specific software controls to avoid some movements or some undesired maneuvers in the detected regions. For example, a haptic "push" from the user input device may be applied to resist or prevent the surgeon from moving the surgical instrument into contact with a structure or tissue to be avoided, or a scaling factor of the surgical system may be adjusted to scale down the movement of the surgical instrument in response to movement of the user input device.

If the user input device at the surgeon console is a haptic interface, modify software parameters to enhance or decrease the force feedback or the exceeding force thresholds Enable an advanced energy device or set/alter settings on an electrosurgical unit that will subsequently be used by the surgeon Automatically activate a fluorescence camera d. Super Image Displaying a portion of a pre-operative image (e.g. a CT or MRI scan) of the relevant region of the patient's anatomy to provide an enhanced/augmented 2D or 3D image in the spot the surgeon is looking at. For example, the displayed image may be one that is more magnified than the real-time camera image, providing the surgeon with a very detailed and "super" image, obtained from the pre-operative images.

All prior patents and applications referred to herein, including for purposes of priority, are incorporated herein by reference.

What is claimed is:

1. A system comprising:
    a camera positionable in a body cavity;
    at least one surgical instrument having a distal end positionable within the body cavity;
    a display;
    an eye tracker;
    at least one processor and at least one memory, the memory storing instructions executable by the at least one processor to:
        cause an image of the body cavity captured by the camera to be displayed in real time on the display;
        based on input from the eye tracker, determine the region of the displayed image being viewed by the user;
        perform, in real time, computer vision analysis of an area of the image determined to correspond to the region being viewed by the user on the display and to, based on the computer vision analysis, identify blood vessels, organs, tissue types, tumors, structures to be avoided by the surgical instrument, or regions to be avoided by the surgical instrument, within the region from image data obtained by the camera;
        obtain information from a database regarding the identified blood vessels, organs, tissue types, tumors, structures to be avoided by the surgical instrument, or regions to be avoided by the surgical instrument, within the body cavity; and
        generate an overlay to alert the user to the identified blood vessels, organs, tissue types, tumors, or structures to be avoided by the surgical instrument, or regions to be avoided by the surgical instrument, and displaying the overlay in real time on the display overlaying the image.

2. The system according to claim 1, where the at least one memory further stores instructions executable by the processor to generate an auditory alert to alert the user to the identified blood vessels, organs, tissue types, tumors, or structures or regions to be avoided.

3. The system according to claim 1, wherein the surgical device is an energy delivery device, a diagnostic device, or a fluorescence camera.

4. The system according to claim 1, where the system includes a user input device, a robotic manipulator carrying a surgical instrument, the robotic manipulator moveable in response to user manipulation of the user input device, and wherein the at least one memory further storing instructions executed by the processor to generate or modify haptic feedback generated at the user input device based on the obtained information.

5. The system according to claim 1, wherein the instructions are executable by the at least one processor to, based on the computer vision analysis, identify blood vessels or organs within the body cavity from image data obtained by the camera and to obtain information from the database regarding the identified blood vessels or organs.

6. The system according to claim 1, wherein the instructions are executable by the at least one processor to, based on the computer vision analysis, identify tumors within the body cavity from image data obtained by the camera, and to obtain information from the database regarding the identified tumors.

7. The system according to claim 1, wherein the instructions are executable by the at least one processor to, based on the computer vision analysis, identify structures or regions to be avoided within the body cavity from image data obtained by the camera, and to obtain information from the database regarding the identified structures or regions to be avoided.

8. The system according to claim 1, wherein the instructions are executable by the at least one processor to, based on the computer vision analysis, identify tissues or tissue types within the body cavity from image data obtained by the camera, and to obtain information from the database regarding the identified tissues or tissue types.

9. The system according to claim 1, wherein the at least one memory further stores instructions executable by the processor to, in response to the obtained information, enable, or modify operational settings for, a surgical device to be used in the body cavity.

10. The system according to claim 1, wherein the overlay is displayed on the display in the region of the displayed image.

11. A system comprising:
a camera positionable in a body cavity;
at least one surgical instrument having a distal end positionable within the body cavity;
a display;
an eye tracker;
at least one processor and at least one memory, the memory storing instructions executable by the at least one processor to:
cause an image of the body cavity captured by the camera to be displayed in real time on the display;
based on input from the eye tracker, determine the region of the displayed image being viewed by the user;
perform, in real time, computer vision analysis of an area of the image determined to correspond to the region being viewed by the user on the display and to, based on the computer vision analysis, identify blood vessels, organs, tissue types, tumors, structures to be avoided by the surgical instrument, or regions to be avoided by the surgical instrument, within the region from image data obtained by the camera; and
generate an overlay to alert the user to the identified blood vessels, organs, tissue types, tumors, structures to be avoided by the surgical instrument, or regions to be avoided by the surgical instrument, and displaying the overlay on the display overlaying the image.

12. The system according to claim 11, wherein the overlay is displayed on the display in the region of the displayed image.

13. The system according to claim 11, wherein the visual alert is at least one of a graphic, icon or text displayed as an overlay on the display.

14. The system according to claim 11, where the system includes a user input device, a robotic manipulator carrying a surgical instrument, the robotic manipulator moveable in response to user manipulation of the user input device, and wherein the at least one memory further storing instructions executed by the processor to generate or modify haptic feedback generated at the user input device based on the obtained information.

* * * * *